United States Patent [19]

Yamauchi

[11] 4,140,120

[45] Feb. 20, 1979

[54] PORTABLE BIDET

[76] Inventor: Akira Yamauchi, 121 Tatsumachi Sasayamacho, Takigun, Hyogo Prefecture, Japan

[21] Appl. No.: 555,048

[22] Filed: Mar. 3, 1975

[30] Foreign Application Priority Data

Oct. 14, 1974 [JP] Japan .............................. 49-124352[U]

[51] Int. Cl.² .............................................. A61M 1/00
[52] U.S. Cl. ............................................ 128/232; 4/7; 128/251
[58] Field of Search ................ 4/7, 110; 128/232, 231, 128/251, 248; 222/209; 137/150, 232

[56] References Cited

U.S. PATENT DOCUMENTS

| 268,805 | 12/1882 | Knight | 128/232 |
| 1,576,128 | 3/1926 | Ballard | 128/231 |
| 2,674,247 | 4/1954 | McLellan | 128/232 |
| 2,839,073 | 6/1958 | Marsh | 137/232 |
| 3,844,284 | 10/1974 | Schoenfeld | 128/232 |
| 3,905,370 | 9/1975 | Lazdowski | 128/232 |

Primary Examiner—Stuart S. Levy
Attorney, Agent, or Firm—Armstrong, Nikaido, Marmelstein & Kobovcik

[57] ABSTRACT

A portable bidet which includes a check valve and plug in its receptacle so that the receptacle which contains washing liquid can readily be restored to its original inflated shape after being constricted, to thereby allow speedy washing of the vagina.

2 Claims, 3 Drawing Figures

PORTABLE BIDET

BACKGROUND OF THE INVENTION

The present invention relates to a portable bidet for washing the vagina. In conventional bidets of this kind, a nozzle protrudes from the head of a receptacle which is made of an elastic material such as rubber and capable of a liquid squirting operation. The nozzle is provided with small holes in its end, and moreover, the base of the nozzle is connected with the inner bottom of the receptacle by means of a suction tube. When the receptacle has been constricted, with the nozzle inserted into the vagina, washing liquid within the receptacle is squirted from the plurality of small holes in the end of the nozzle through the suction tube to thereby allow the washing of the vagina. However, the receptacle takes a long time (approximately five minutes) to become completely inflated back to its original shape after being constricted. As a result, quick washing can not be achieved. The present invention is directed to the removal of the foregoing disadvantage of the conventional portable bidets.

SUMMARY OF THE INVENTION

In the portable bidet of the present invention, the receptacle has an aperture in its side wall. A small tube is inserted into this aperture and provided with a tongue member on its inside end to thereby allow the small tube to act as a check valve. If the check valve is not covered with a plug means as the receptacle of the bidet is constricted and thereafter released from constriction, the receptacle is readily restored to its original expanded state because the air rushes into the receptacle through the fluid flow passage formed by the small tube.

BRIEF DESCRIPTION OF THE DRAWING

The accompanying drawing shows an embodiment of the present invention relating to a portable bidet, in which.

DETAILED DESCRIPTION OF THE PREFERRED EMBODIMENT

Figure 1:
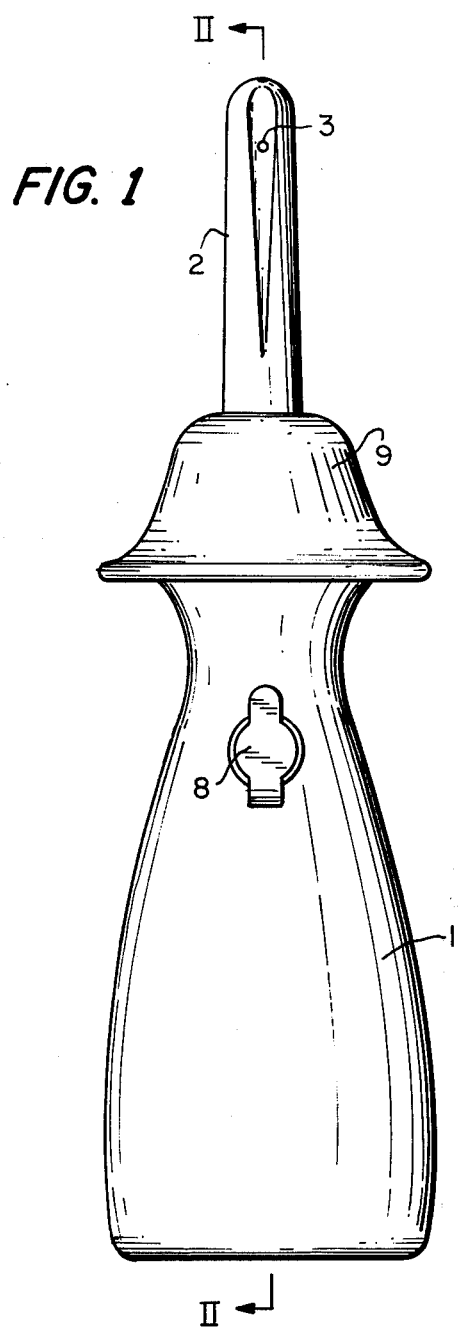
FIG. 1 is a front view.
Figure 2:
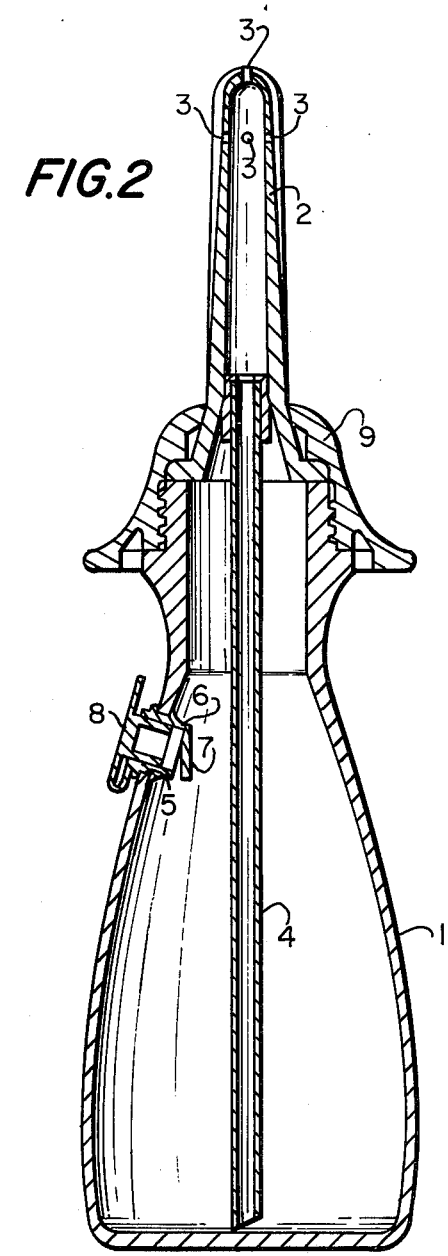
FIG. 2 is a sectional view taken along the line II—II of FIG. 1.

A preferred embodiment of the present invention will now be described with reference to the accompanying drawing.

An aperture 5 is made preferably in an upper portion of the side wall of a receptacle 1 and has a small tube 6 inserted therein. The small tube 6 is provided with a tongue member 7 on its inside end to thereby allow the small tube to act as a valve. That is to say, the tongue member 7 is connected at its upper end to the small tube 6 so that it operates as a hinge means thereby opening and closing the liquid flow passage of the small tube 6. Therefore, this small tube 6 and tongue 7 form a check valve allowing flow into the receptacle through tube 6, but preventing flow from the receptacle through tube 6.

In the figures, 4 is a suction tube connecting the base of the nozzle 2 with the inner bottom of the receptacle 1. Furthermore, 8 is a plug means inserted into the small tube 6, and 9 is a cap means screwed on the top of the receptacle 1. This cap means 9 and the receptacle 1 connect to a nozzle 2, which is a separate member.

As a matter of course, the bidet according to the present invention can be used, with the plug means 8 inserted into the small tube 6. However, even if the receptacle 1 is constricted without inserting the plug means 8 into the small tube, fluid within the receptacle 1 does not flow out from the small tube 6, since the tongue member 7 is brought into close contact with the small tube 6 by means of the pressure of said fluid to thereby block the fluid flow passage of the small tube 6.

If the receptacle 1 is released from constriction, with the plug means 8 not inserted in tube 6, the receptacle 1 is readily restored to its original expanded state, because the air rushes into the receptacle 1 through the fluid flow passage of the small tube 6. When the nozzle 2 has been inserted into the vagina, the vagina is substantially in a vacuum state since the upper surface of the cap means 9 makes close contact with the body. As a result, the bidet of the present invention achieves the immediate restoration of the receptacle to its original inflated shape, while the conventional bidets take a considerable time to restore the receptacles to their original expanded state. The effect of the immediate restoration of the receptacle has experimentally and satisfactorily been confirmed.

When the receptacle 1 is released from constriction and plug 8 is not inserted in passage 6, used and contaminated liquid after being squirted from the nozzle 2 does not flow back into the receptacle 1, because the air flows into the receptacle 1 through the small tube 6 and fills the receptacle, as described in the foregoing.

Figure 3:
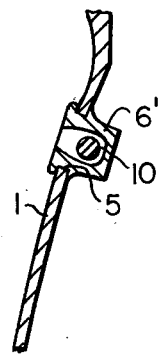
FIG. 3 shows a modification of valve construction essential to the bidet of the present invention.

Even if a small sphere member 10 is used as shown in FIG. 3 instead of the tongue member 7 to open and close the fluid flow passage of the small tube 6', said sphere member 10 provides the same effect as the tongue member 7.

In the present invention, since the receptacle 1 is arranged to be quickly restored to its original inflated state after being constricted, speedy washing of the vagina can be obtained.

If the receptacle 1 is constricted, with the plug means 8 inserted into the small tube 6, used liquid squirted from the nozzle 2 can be reversed into the receptacle 1 although the constricted receptacle is slow in restoration to its original expanded shape. Therefore, the same liquid can be circulated between the bidet and the vagina as in conventional bidets according to a place and manner in which the bidet is used.

Obviously, numerous modifications and variations of the present invention are possible in the light of the foregoing teachings. It is therefore to be understood that within the scope of the appended claims the invention may be practiced otherwise and as specifically described herein.

I claim:

1. In a portable bidet comprising a nozzle having a plurality of small holes therein and a receptacle connected to said nozzle such that when said receptacle is constricted fluid in said receptacle flows from said nozzle, the improvement comprising a check valve means including a tube passing through the wall of said receptacle, a tongue member hinged to the end of said tube within said receptacle, and a plug means for insertion into said tube means to thereby block said tube means wherein said check valve means enables the rapid expansion of said receptacle after constriction.

2. In a portable bidet comprising a nozzle having a plurality of small holes therein and a receptacle connected to said nozzle such that when said receptacle is constricted fluid in said receptacle flows from said nozzle, the improvement comprising a check valve means in the wall of said receptacle said check valve means comprising a tube passing through the wall of said receptacle, a sphere within said tube said sphere being movable between first and second positions said first position allowing fluid to enter said receptacle through said tube and said second position preventing fluid from flowing from said receptacle through said tube, wherein said check valve means enables the rapid expansion of said receptacle after constriction.

* * * * *